United States Patent [19]
Denes et al.

[11] Patent Number: 6,096,564
[45] Date of Patent: Aug. 1, 2000

[54] PLASMA-AIDED TREATMENT OF SURFACES AGAINST BACTERIAL ATTACHMENT AND BIOFILM DEPOSITION

[75] Inventors: Agnes Reka Denes; Eileen B. Somers; Amy C. Lee Wong; Ferencz Sandor Denes, all of Madison, Wis.

[73] Assignee: Wisconsin Alumni Research Foundation, Madison, Wis.

[21] Appl. No.: 09/318,355

[22] Filed: May 25, 1999

[51] Int. Cl.[7] .................................................. H01L 21/00
[52] U.S. Cl. ................................................. 438/1; 438/800
[58] Field of Search ............................... 438/1, 798, 800, 438/9, 795; 75/10.1, 10.19; 134/1.1; 216/67, 69; 427/570

[56] References Cited

U.S. PATENT DOCUMENTS

| | | |
|---|---|---|
| 3,870,610 | 3/1975 | Baird et al. . |
| 4,536,179 | 8/1985 | Anderson et al. . |
| 4,632,842 | 12/1986 | Karwoski et al. . |
| 4,676,195 | 6/1987 | Yasui et al. . |
| 4,804,431 | 2/1989 | Ribner et al. ............................ 156/345 |
| 5,000,831 | 3/1991 | Osawa et al. . |
| 5,034,265 | 7/1991 | Hoffman et al. . |
| 5,091,204 | 2/1992 | Ratner et al. . |
| 5,281,315 | 1/1994 | Krapivina et al. . |
| 5,920,799 | 7/1999 | Graces et al. ............................ 438/798 |

OTHER PUBLICATIONS

Gabriel P. Lopez, et al., "Glow Discharge Plasma Deposition of Tetraethylene Glycol Dimethyl Ether for Fouling-Resistant Biomaterial Surfaces," Journal of Biomedical Materials Research, vol. 26, 1992, pp. 415–439.

Buddy D. Ratner, "Plasma Deposition for Biomedical Applications: A Brief Review," J. Biomater. Sci. Polymer Edn., vol. 4, No. 1, 1992, pp. 3–11.

Krister Holmberg, et al., "Effects on Protein Adsorption, Bacterial Adhesion and Contact Angle of Grafting PEG Chains to Polystyrene," Contact Angle, Wettability and Adhesion, Ed. K.L. Mittal, 1993, pp. 813–827.

Buddy D. Ratner, "Surface Modification of Polymers: Chemical, Biological and Surface Analytical Challenges," Biosensors & Bioelectronics, vol. 10, 1995, pp. 797–804.

Erika E. Johnston, et al., "XPS and SSIMS Characterization of Surfaces Modified by Plasma Deposited Oligo(glyme) Films," Suface Modification of Polymeric Biomaterials, Edited by B.D. Ratner and D.G. Castner, Plenum Press, New York, 1996, pp. 35–44.

*Primary Examiner*—Charles Bowers
*Assistant Examiner*—Craig Thompson
*Attorney, Agent, or Firm*—Foley & Lardner

[57] ABSTRACT

Passivation of bacterial biofilm exposed surfaces is carried out utilizing cold-plasma treatments. Exposure of a substrate with biological contamination thereon to an oxygen plasma sterilizes and cross-links the biological contamination into a form which is resistant to further adhesion of bacteria and other biomaterials while cleansing and sterilizing areas of the substrate that are not covered by the biofilm. A second step may be carried out to plasma mediate the deposit of an anti-fouling film using components that will provide macromolecular networks on the substrate with a desired structure which is resistant to bacterial adhesion.

38 Claims, 8 Drawing Sheets

PLASMA-AIDED TREATMENT OF SURFACES AGAINST BACTERIAL ATTACHMENT AND BIOFILM DEPOSITION

This invention was made with United States government support awarded by the following agency: NSF Grant No. 8721545. The United States government has certain rights in this invention.

FIELD OF THE INVENTION

This invention pertains generally to the field of plasma processing of materials and to treatment of surfaces to sterilize the surfaces and to protect the surfaces against bacterial attachment and biofilm deposition.

BACKGROUND OF THE INVENTION

Bacterial deposits on the surfaces of food processing equipment can lead to potential contamination of food products. Bacterial deposits on medical devices such as implants, catheters and intraocular lenses also present the potential for infection when in contact with patients and medical personnel. Consequently, good hygiene standards require that food processing equipment be thoroughly cleaned between uses and that medical and dental equipment be sterilized if possible or at least, for non-surgical instruments, thoroughly cleaned before use. Other surfaces proximate to food processing or medical equipment, such as flooring, walls, tiles, conveyor belts, drains, and packaging, also should be regularly cleaned. Nonetheless, the potential always exists for residual bacterial deposits or for the incidental growth of bacteria on cleaned surfaces, particularly after contact with biological materials as encountered in food processing, e.g., blood, fats, and proteins. For equipment that cannot be thoroughly sterilized between uses, such as most food processing equipment, the potential exists for residual bacteria surface deposits because of the tenacious adherence of bacterial biofilms to the material of the processing equipment, commonly stainless steel but also often including other metals and polymers. Biofilms are communities of microorganisms adhering to surfaces of substrates, usually within a matrix of extracellular polymeric substances. Contamination of biological origin (hereafter biological contamination) on surfaces can include biofilms, blood, proteins, fats, oils, or combinations of such materials.

It would be desirable to treat and passivate the surfaces of the materials commonly used in food processing equipment, such as stainless steel, to reduce the ability of biological contamination such as bacterial biofilm to adhere to the surface. It is known that neutral polymers like poly(ethylene glycol) (PEG), polysaccharides such as ethyl (hydroxyethyl)-cellulose, and polyglucose dextran, deposited or grafted as thin layers on various surfaces, substantially reduces protein adsorption. This capability is believed to be related to the predominant presence of C—O linkages in these synthetic and natural polymeric structures. However, it has been difficult to carry out a practical treatment of food processing equipment and many types of medical equipment to provide surface treatments that are both effective against bacterial biofilm deposit and durable.

SUMMARY OF THE INVENTION

In accordance with the present invention, passivation of surfaces with biological contamination thereon is carried out utilizing plasma treatments. The invention utilizes cold-plasma mediated conversion of biological contamination into a highly cross-linked three-dimensional macromolecular network with a poly(ethylene oxide) or poly(ethylene glycol) (PEG) type structure composed predominantly of C—O—C linkages. Where the substrate surface has a sufficient layer of biological contamination thereon, the resulting passivated layer of biological contamination after plasma treatment is both sterilized and cross-linked into a polymer form which is resistant to further adhesion of bacteria and other biological materials. Where the substrate surface has only a very thin layer of biological contamination, as is often the case, a two-step process is carried out in accordance with the invention, involving a first reactive plasma treatment to sterilize the surface and cross-link the deposits of biological contamination followed by a plasma mediated deposit of an anti-fouling film. Such plasma enhanced depositions of anti-fouling films are carried out using components which will provide macromolecular networks with the desired structures (for example, PEG oligomers, crown ethers, etc.). The reactive plasma treatment before the deposition of a specific monomer origin macromolecular network enhances the adhesion of the anti-fouling film to the substrate due to the presence of an active (e.g., having the presence of free radical species) cross-linked intermediate layer.

In carrying out the reactive plasma treatment of the invention, a substrate having a surface with a biological contamination deposit thereon is enclosed in a reaction chamber and the reaction chamber is evacuated to a base level. A selected oxygen flow rate and pressure is established in the chamber, the plasma is ignited in the gas in the chamber, and the substrate is exposed to the plasma for a selected period of time to form a cross-linked film without etching the film off the surface, after which the substrate may be removed from the chamber. In accordance with the invention, it is found that the oxygen plasma treatment converts the surface biological contamination into a highly cross-linked three-dimensional network composed predominantly of C—O—C linkages which resist adsorption by bacteria and proteins. Such chemical bonds are also the major components of PEG and polysaccharides, which are known to be resistant to protein and particle adsorption.

Where the biological contamination on the substrate surface is not sufficient in itself to provide a complete film over the surface after the initial reactive plasma treatment, a second plasma exposure may be carried out within a reactor chamber by introducing an appropriate monomer into the chamber and inducing a plasma in the monomer gas to form a cross-linked film on the substrate. Various cross-linkable compounds, referred to herein as "monomer sources," may be utilized for providing the cross-linked network with C—O—C linkages over the exposed substrate surface and the previously cross-linked biological contamination film.

In addition, the present invention may be utilized to plasma deposit a cross-linked macromolecular network having C—O—C linkages on relatively clean surfaces to provide desirable resistance to bacterial adhesion. In accordance with the invention, low volatility monomer source compounds, particularly crown ethers, which provide a strongly adhering network of C—O—C linkages, may be utilized by appropriate heating and temperature control of the monomer reservoir, plasma reactor and monomer supply tubing. By appropriate temperature control of the reactor and the substrate being treated, cross-linked films of such materials may be deposited from the plasma without significant condensation of the monomer on the substrate. If desired, an initial sterilization of the surface with an oxygen plasma may be carried out as described above, or by plasma etching using, for example, the noble gases, nitrogen, $CF_4$, $NH_3$, etc., in a conventional manner.

Metallic (e.g., stainless steel), other inorganic (e.g., ceramics), and polymeric substrates (e.g., rubber, polypropylene, etc.) can be passivated by the plasma treatment in accordance with the invention. Due to the energy levels of the plasma species (including electrons, photons, and charged and neutral atomic and molecular species), which are comparable to the chemical bond energies of organic molecules, the plasma induced chemistry in accordance with the invention provides an ideal surface modification process. The active species can ablate the substrate surface structures or induce chemical modifications in the surface layers which cannot be achieved by conventional wet chemical approaches. The active species of the plasma discharge penetrate only about 100 Angstroms into the surface layers, and, consequently, the energy requirements for surface modifications are minimal. With appropriate reactor and electrode configurations, three-dimensional, irregularly shaped and large objects can be uniformly plasma treated. The plasma treatment also has the advantage of inherently sterilizing the plasma discharge exposed surfaces. A variety of plasma discharge apparatus can be employed in accordance with the invention. Capacitively or inductively coupled, electrode or electrodeless discharges can be utilized, as well as low and high density plasma environments. Radio frequency (RF) discharges are preferred because of the insulating nature of the biofilm and biological contamination on the substrate surface.

The invention thus provides a passivated, sterilized substrate surface having a film formed thereon with a PEG type structure of C—O—C linkages which is resistant to adhesion by bacteria, proteins, and polysaccharides.

Further objects, features and advantages of the invention will be apparent from the following detailed description when taken in conjunction with the accompanying drawings.

DETAILED DESCRIPTION OF THE INVENTION

Biological contamination on food processing surfaces is a potential source of bacterial contamination of foods and can result in decreased shelf life or transmission of disease. The possible presence of biological contamination on medically related devices, such as surgical and medical instruments, implants and prosthetics is also of serious concern. It would also be desirable to treat surfaces of a variety of other materials, e.g., upholstery fabrics, plastic food packaging films, and so forth, to make them resistant to the deposit and adhesion of bacteria and other biological materials. The present invention effectively serves to sterilize the surfaces of such substrates, to convert the biological contamination deposits on such surfaces to inert, cross-linked films that are resistant to bacterial adhesion and attack, and optionally and preferably to coat the passivated surfaces with a strongly adherent protective cross-linked film that is resistant to deposits of biological contamination and to bacterial attack.

The process of surface treatment in accordance with the invention utilizes cold-plasma processing techniques. Cold plasmas are non-thermal and non-equilibrium plasmas versus hot plasmas which are thermal or equilibrium plasmas. In a cold plasma, the kinetic energy of the electrons is high while the kinetic energy of the atomic and molecular species are low; in a hot plasma the kinetic energy of all species is high and organic materials would be damaged or destroyed in a hot plasma. The substrates to be treated are enclosed within a plasma reactor and exposed to an oxygen plasma discharge for a period of time selected to kill living bacterial cells on the surface and thus sterilize the surface, to ablate and activate areas of the substrate surface which are not covered by biofilm, and to convert the biological contamination including killed bacteria into a strong cross-linked macromolecular network film which is itself highly resistant to further adhesion by microorganisms and which is resistant to attack by bacteria. In appropriate circumstances where the biological contamination covers the surface of the substrate, the biological contamination itself may be converted by this process to a cross-linked film that provides adequate protection of the surface against subsequent bacterial adhesion and attack.

In a second phase of the process, which may be utilized where the biological contamination layer is very thin, plasma mediated deposit of anti-fouling films onto the previously passivated surface of the substrate is carried out.

A variety of substrate materials may be treated in accordance with the present invention. Examples of these include polymers such as silicone rubber, Buna N rubber, poly (ethylene), polystyrene, polypropylene, poly(ethylene terephthalate), poly(methyl methacrylate), cellophane, Teflon®, polyurethane; metals such as stainless steel, titanium- and cobalt-based alloys; and ceramics.

The preferred initial sterilization plasma treatment in accordance with the invention is carried out utilizing oxygen gas plasma. If desired, the plasma may also contain inert gases such as argon.

A variety of monomer sources may be utilized in accordance with the invention in carrying out the plasma mediated formation of cross-linked surface films that are resistant to bacterial adhesion and attack. Suitable monomer sources are those that provide a poly(ethylene oxide) or essentially similar poly(ethylene glycol) type structure when vaporized and plasma deposited on a substrate. Examples of compounds which may utilized in the plasma coating process of the invention include ethers such as 12-crown-4, 15-crown-5, tri(ethylene glycol) dimethyl ether, tetra(ethylene glycol) dimethyl ether, tri(ethylene glycol) divinyl ether; triethylene glycol; poly(ethylene glycol) of various molecular weights; ethylene oxide; propylene oxide; dioxane; polysaccharides such as dextrin; acrylonitrile; 2-hydroxyethyl methacrylate; and quaternary ammonium compounds.

Plasma functionalization of the surfaces as well as plasma-depositions can be carried out under various external plasma parameters. The following are exemplary: pressure range: 50–1000 mTorr; power: 25–1000 W, treatment time: 0.5 min.–1 hour (or longer); reactor temperature: 25–500° C.; monomer reservoir temperature: as required by the volatility of the monomer. Non-equilibrium plasma processes can also be developed under high (atmospheric) pressure conditions. Corona or barrier discharge type installations are adequate, for instance, for surface treatments.

Figure 1:
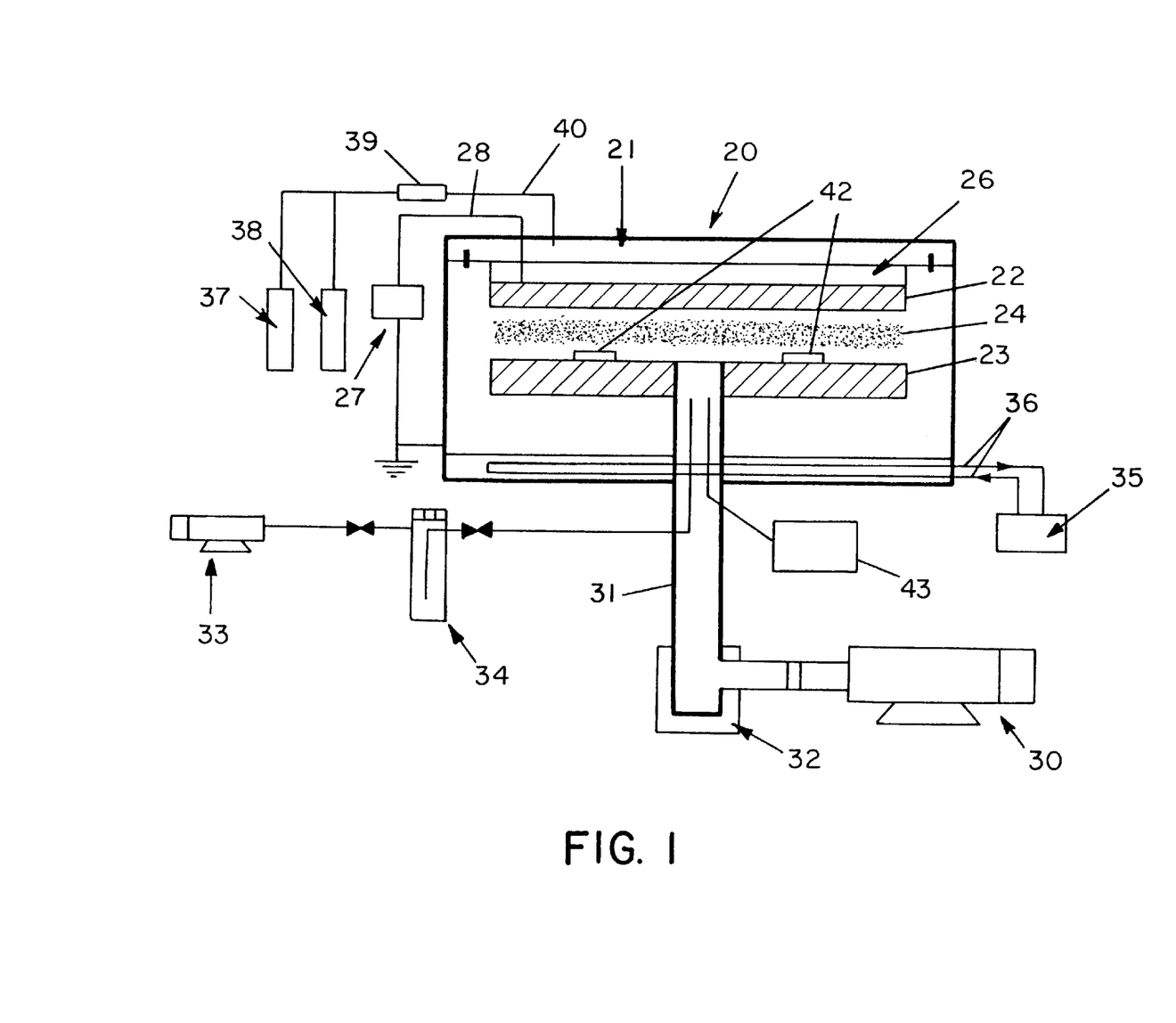
FIG. 1 is a schematic diagram of an exemplary capacitively-coupled cold-plasma reactor system that may be utilized in carrying out the invention.
Figure 2:
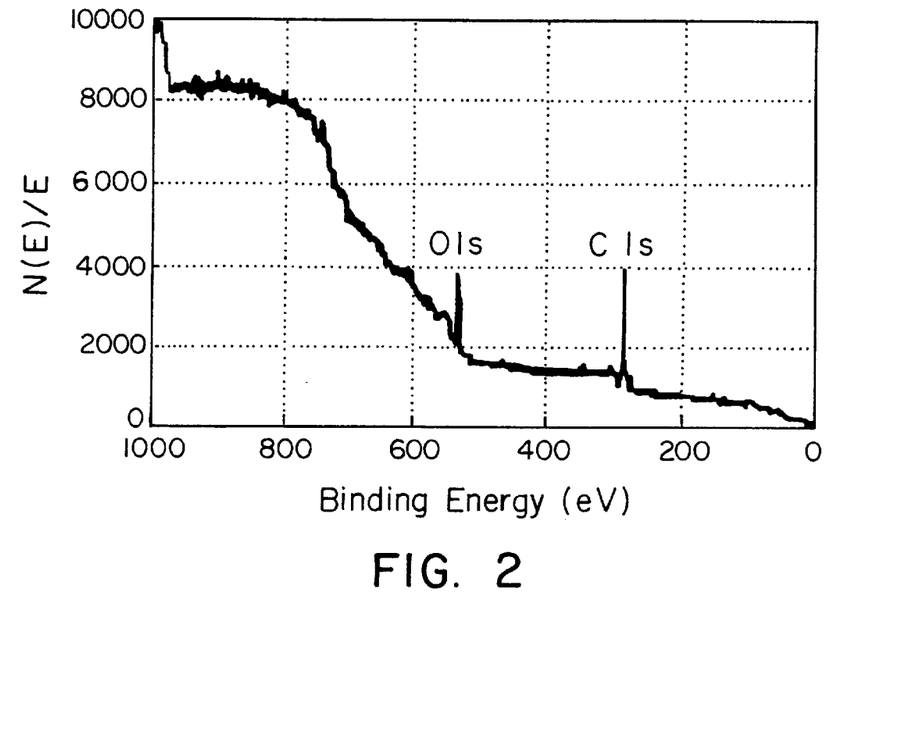
FIG. 2 is a survey ESCA spectrum of untreated stainless steel.
Figure 3:
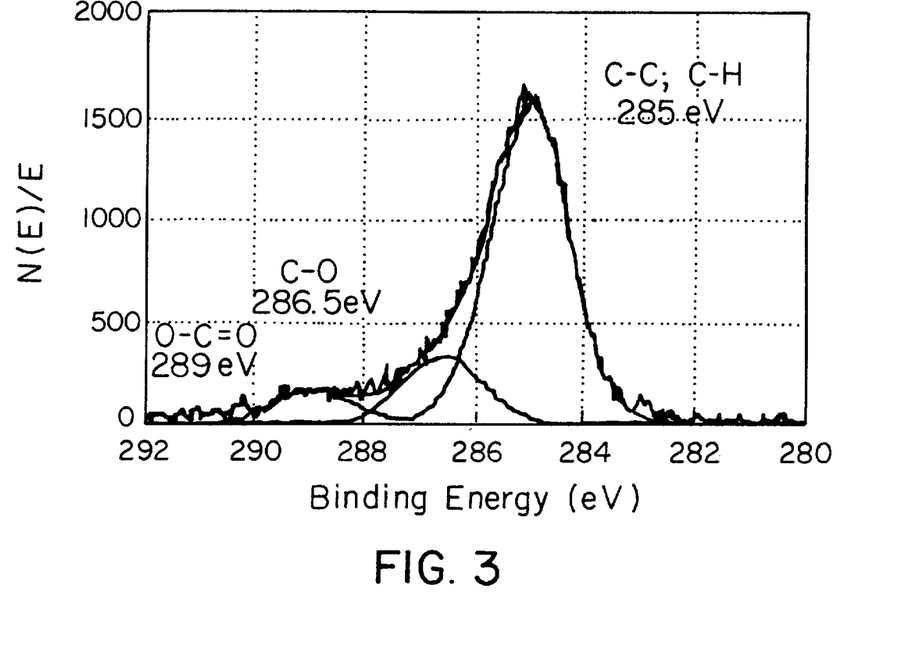
FIG. 3 is a high resolution C1s ESCA spectrum of untreated stainless steel.
Figure 4:
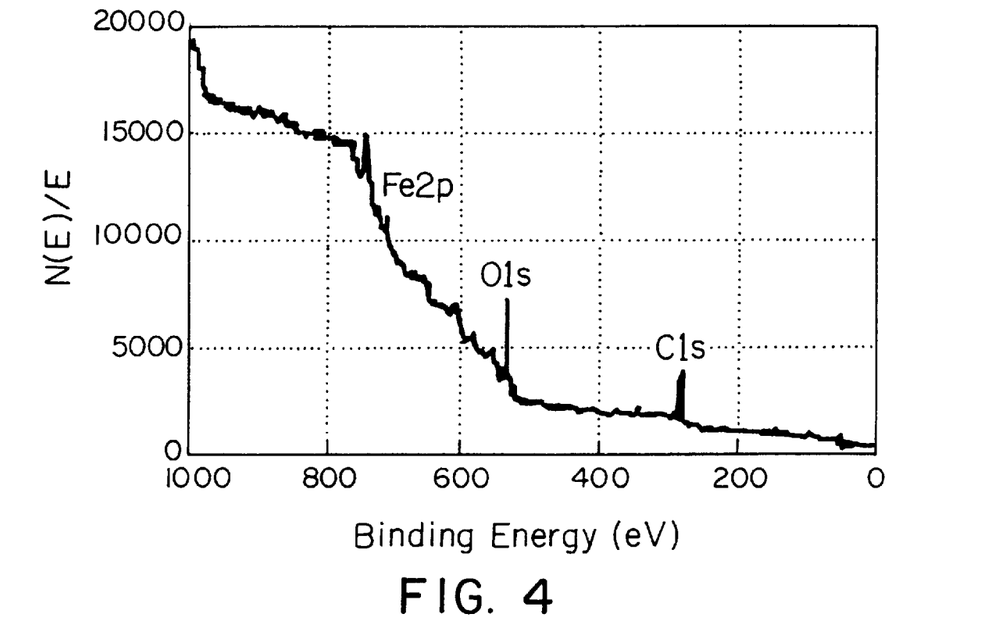
FIG. 4 is a survey ESCA spectrum of a stainless steel substrate as in FIGS. 2 and 3 after 20 minutes of $O_2$-plasma treatment in accordance with the invention.
Figure 5:
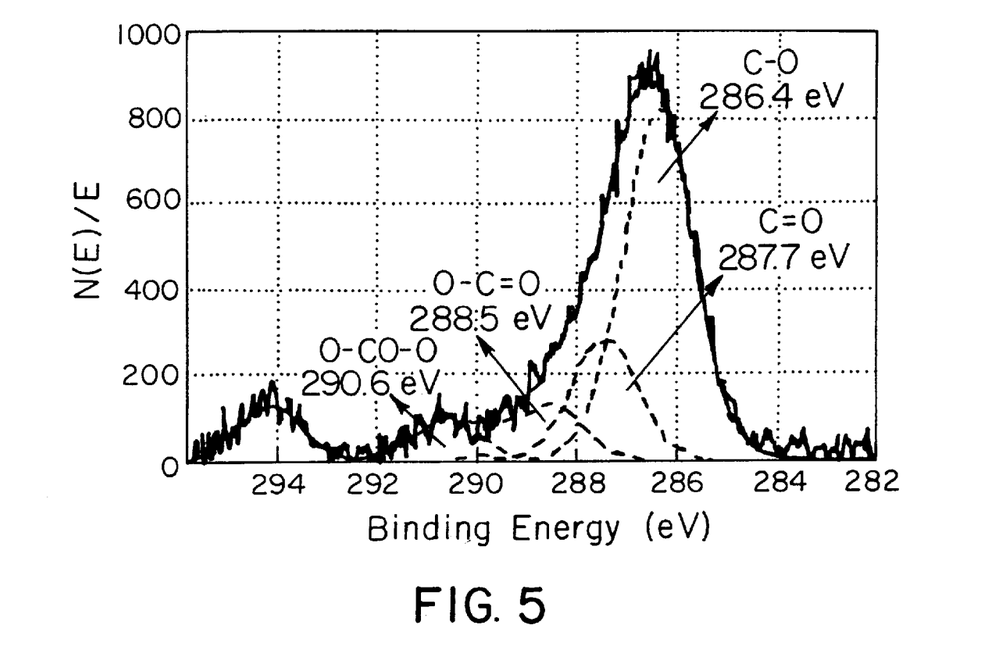
FIG. 5 is a high resolution C1s ESCA spectrum of a stainless steel substrate surface after plasma treatment as in FIG. 4.

An example of a cold-plasma reactor system that may be utilized in accordance with the invention is shown schematically at 20 in FIG. 1. The reactor system 20 includes a gas mixing reactor chamber 21 which encloses an upper electrode 22 and a lower electrode 23 between which a plasma reaction region 24 is established. An electrical insulation disk 26 is mounted between the walls of the gas mixing chamber 21 and the upper electrode 22. A radio frequency power supply 27 is connected by lines 28 to the upper electrode 22, while the lower electrode 23 is grounded, as are the walls of the gas mixing chamber 21. A high capacity mechanical vacuum pump 30 is connected by a conduit 31 to the interior of the chamber 21 to selectively evacuate the chamber (a liquid nitrogen trap 32 may be utilized to capture condensates). A further high vacuum mechanical vacuum pump 33 may be connected through another liquid nitrogen trap 34 (for collecting plasma-generated molecular mixtures) to the interior of the chamber 21. An electrical heater 35 is connected to wires 36 to selectively heat the interior of the chamber. A reaction gas reservoir 37 and a monomer reservoir 38 are connected through a control valve 39 by conduits 40 to the interior of the chamber 21 to allow selective introduction of the reaction gas or the monomer into the evacuated chamber.

In use, a sealable door (not shown in FIG. 1) is opened to allow the substrate materials illustrated at 42 in FIG. 1 to be inserted onto and supported by the lower electrode 23 (and thus also grounded). The door is then closed and sealed, and the high capacity vacuum pump 30 is operated to rapidly withdraw the air within the chamber. The lower capacity, low pressure vacuum pump 33 is then utilized to draw the interior of the chamber down to the desired vacuum base level. When that vacuum level is reached, the valve 39 is operated to selectively allow introduction of the $O_2$ reaction gas from the reservoir 37 into the reaction chamber at a controlled flow rate to reach a selected gas pressure, and the RF power supply 27 is turned on to provide capacitive coupling between the upper and lower electrodes 22 and 23 and the gas between them to ignite and sustain the plasma in the region 24 between the electrodes. The plasma is maintained at a desired pressure level determined by the introduction of gas from the reactor 37 for a selected period of time, with a pressure gauge 43 being utilized to measure the pressure and control it. After a selected period of oxygen plasma treatment time, the RF power supply 27 is turned off, the interior of the chamber 21 is repressurized to atmospheric pressure and the substrate workpieces 42 are removed. Alternatively, the workpieces 42 may be left in place and the oxygen atmosphere within the chamber removed by the vacuum pumps 30 and 33, followed by introduction of the monomer gas from the reservoir 38 into the interior of the chamber and reapplication of power from the power supply 27 (or another power supply) to the electrodes 22 and 23 to establish a plasma in the monomer gas between the electrodes in the space 24. The workpieces 42 are then subjected to the polymer film producing plasma for a selected period of time, after which the power supply 27 is turned off, the interior of the chamber is repressurized to atmospheric, and the door opened and the workpieces 42 removed. Of course, a separate plasma reactor may be utilized to carry out the polymer film formation process. The advantages of the use of a single reactor versus two separate reactors are that samples retain their sterilized state during plasma treatment, possible contamination during moving of samples is avoided, and the process is more time and energy efficient.

The time of initial oxygen plasma treatment, the pressure level, and the energy coupled to the plasma are selected to cause cross-linking of the biological contamination film on the substrate surface without etching the film off the surface. Fifteen minutes is a typical plasma treatment time. It is noted that application of the oxygen plasma treatment to the surface at sufficiently high power for a sufficient period of time will essentially ablate or etch away all of the biological contamination film, a conventional way to sterilize the surface. However, in accordance with an aspect of the invention the plasma is applied for a selected time under conditions that do not remove the contamination film but convert it to the desired cross-linked structure.

The reactor system of FIG. 1 is exemplary of the plasma apparatus that may be utilized to carry out the invention. Any of the various standard types of plasma discharge apparatus configurations can be used in accordance with the invention. The plasma discharges can be capacitively or inductively coupled, with electrodes or electrodeless, under low or high density plasma environments. An example of a suitable inductively coupled plasma reactor is discussed in K. R. Kamath, et al., Journal of Biomaterial Sci. Polymer Edn., Vol. 7, No. 11, pp. 977–988, 1996. Radio frequency (RF) discharges are preferred because of the insulating nature of the biofilm.

The following are examples of a plasma-induced modification technique in accordance with the invention utilizing 40 kHz and 13.56 MHz (having pulsing capability) RF power supplies, and a capacitively coupled (parallel plate 20 cm diameter, disk-shaped stainless steel electrodes 22 and 23), stainless steel reactor chamber 21. The characteristics of the treated workpieces may be analyzed using various standard analysis techniques such as electron spectroscopy for chemical analysis (ESCA), attenuated total reflectance-Fourier transform infrared spectroscopy (ATR-FTIR), atomic force microscopy, scanning electron microscopy and water contact angle analysis.

Stainless steel substrate samples are placed on the lower, grounded electrode 23, and the reactor is then vacuumed to base pressure level. In the next step the oxygen flow rate and/or the pressure of the selected plasma gases is established in the chamber, and the plasma is ignited and sustained at the selected RF-power and gas pressure. At the end of the plasma exposure the samples are removed and subjected to surface-analytical investigation. The external plasma parameters used during the treatments were: plasma gas: oxygen; base pressure: 20 mTorr; flow rate oxygen: 2–25 sccm; pressure in the presence of plasma: 100–300 mTorr; RF-power 100–400 W; treatment time: 1–30 minutes.

Figure 6:
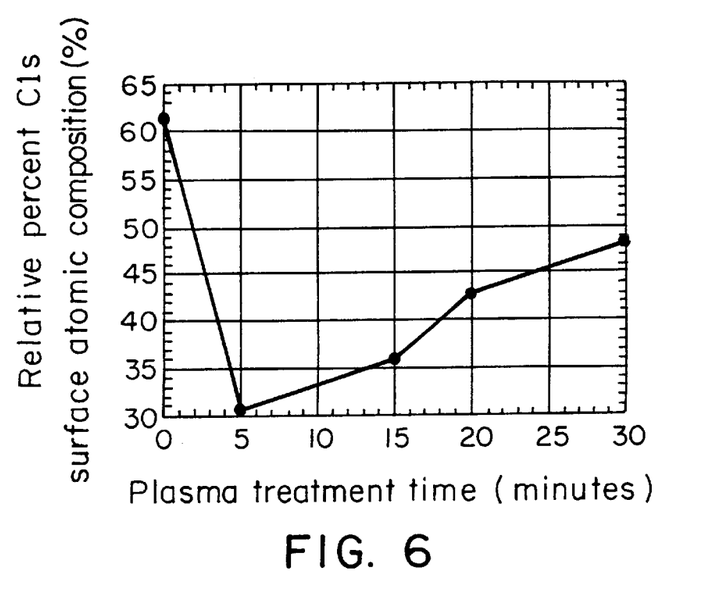
FIG. 6 is a graph illustrating the relative percent C1s surface atomic composition as a function of plasma treatment time.
Figure 7:
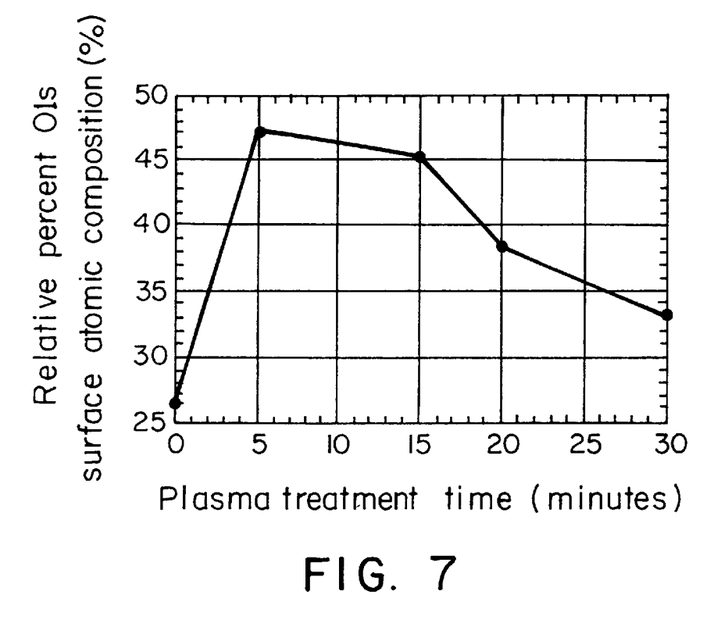
FIG. 7 is a graph illustrating relative percent O1s surface atomic composition as a function of plasma treatment time.
Figure 8:
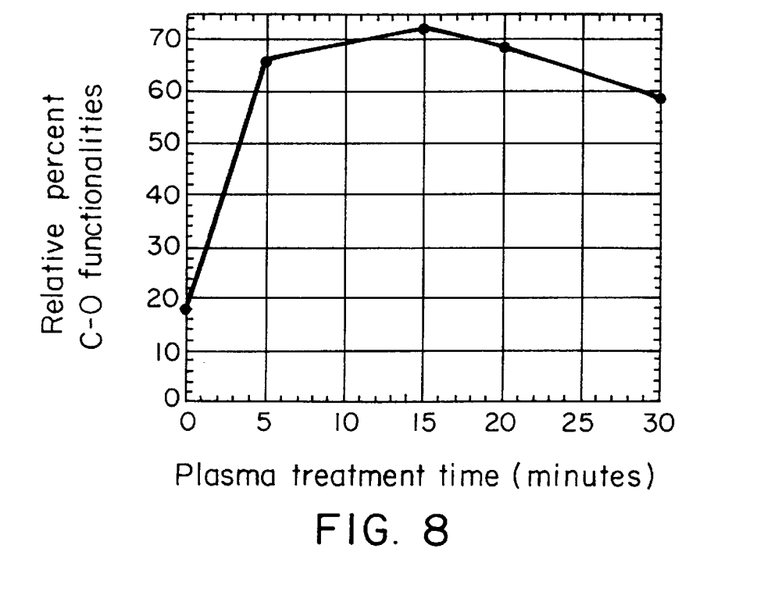
FIG. 8 is a graph illustrating the influence of treatment time on the relative percent surface atomic composition of C—O functionalities.

The comparative survey and high resolution ESCA spectra of unmodified stainless steel (SS) samples and of the same samples exposed for 20 minutes to $O_2$-plasma at 40 kHz are presented in FIGS. 2 and 3 and FIGS. 4 and 5, respectively. One can observe the presence of an organic layer on the surface of the unmodified stainless steel samples, based on carbon (62%) and oxygen (27%) atoms. The organic films undergo a dramatic change in the relative atomic composition attributable to the oxygen-plasma-induced chemistry as shown in FIGS. 6 and 7. The oxygen content of the films increases substantially, reaching 37% after 20 minutes of treatment, while the carbon content decreases accordingly (43%). It also can be observed that an extremely intense C—O (286.4 eV) peak characterizes the spectrum as a result of the plasma exposure and that the non-equivalent C1s functionalities incorporate the O—CO—O bonds (290.6 eV) (see FIGS. 4 and 5) in addition to the C—O, and O=C—O (288.5 eV) linkages. The presence of high surface concentration C—O peaks can be observed on all samples.

These results indicate that the lowest carbon and the highest oxygen concentrations are achieved in the 5–15 minutes plasma-exposure interval. In addition, the relative atomic composition diagrams of FIGS. 6 and 7 indicate the development of two distinct and competitive processes: (1) At short plasma-treatment times a strong oxidation mechanism dominates the plasma chemistry (0–5 minutes), and (2) during longer plasma-exposures the ablation reactions will be more and more intense. This clearly can explain the presence of minimal (C1s) and maximal (O1s) zones in the diagrams. The early oxidation of the organic film gradually is overtaken by an ablation process which at longer treatment times simultaneously removes the oxidized layers.

The treated samples may then have a macromolecular film formed thereon, by, e.g., 13.56 MHz pulsed plasma deposition of PEG-type macromolecular networks. Due to the low volatility of the starting compounds (e.g. 12-crown ether-4 and tri(ethylene glycol) dimethyl ether) the RF-capacitively coupled plasma reactor 50 shown in FIG. 13 may be utilized, as described further below. The plasma reactor 50 is provided with thermostating capabilities both for the entire reaction chamber and for the monomer feeding supply in a 25–500° C. temperature range.

Experiments in the area of pulsed-plasma deposition processes indicate that the molecular fragmentation and, consequently, the chemical nature of the nascent plasma-deposited layers can be controlled by selecting the appropriate pulsed-plasma parameters. Accordingly, tri(ethylene glycol) dimethyl ether and 12-crown-4-ether precursors were processed under 13.56 MHz, pulsed-plasma conditions for the deposition of PEG-type macromolecular layers. Typical pulse conditions are 30% and 50% duty cycle and 500 $\mu$s pulse period, although other duty cycles and pulse periods may be utilized.

Figure 9:
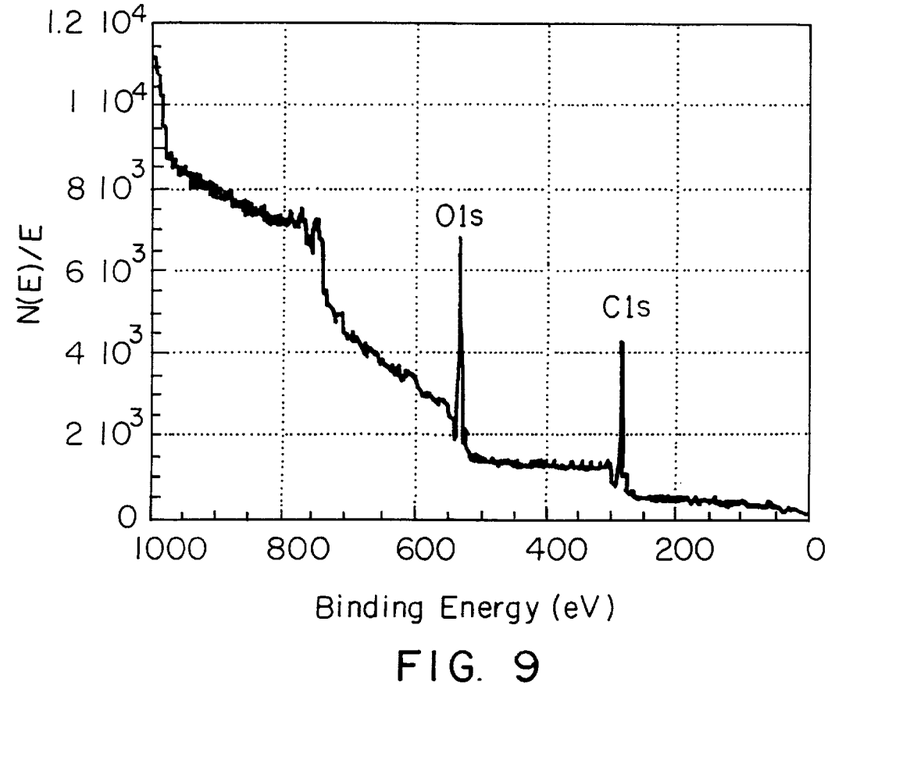
FIG. 9 is a survey ESCA spectrum of 12-crown-4-ether-plasma coated stainless steel in accordance with the invention.
Figure 10:
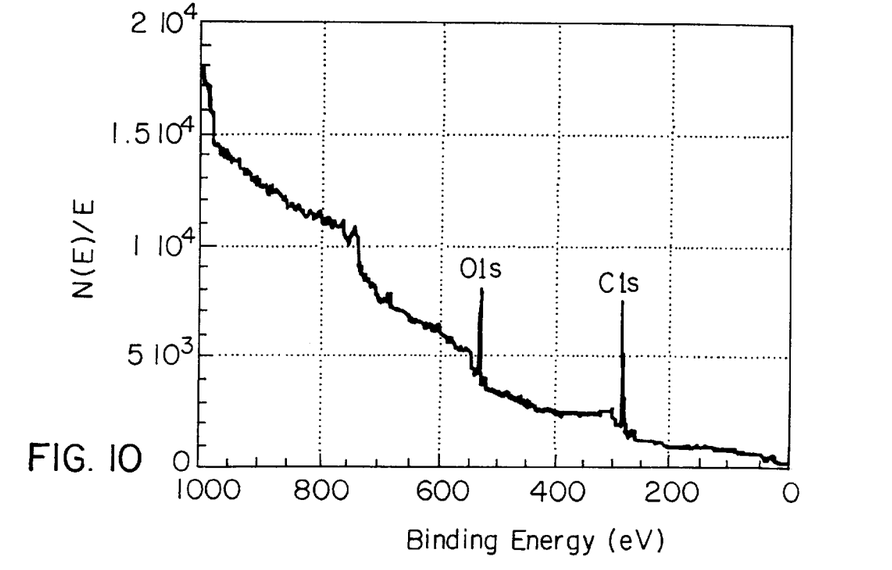
FIG. 10 is a survey ESCA spectrum of tri(ethylene glycol) dimethyl ether-plasma coated stainless steel in accordance with the invention.
Figure 11:
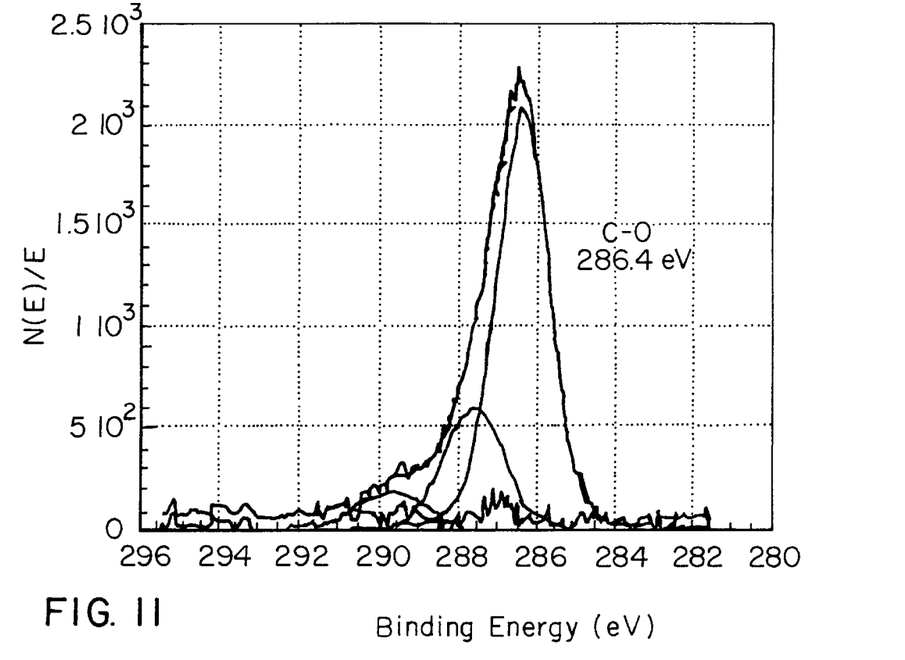
FIG. 11 is a high resolution C1s ESCA spectrum of tri(ethylene glycol) dimethyl ether-plasma coated stainless steel as in FIG. 10.
Figure 12:
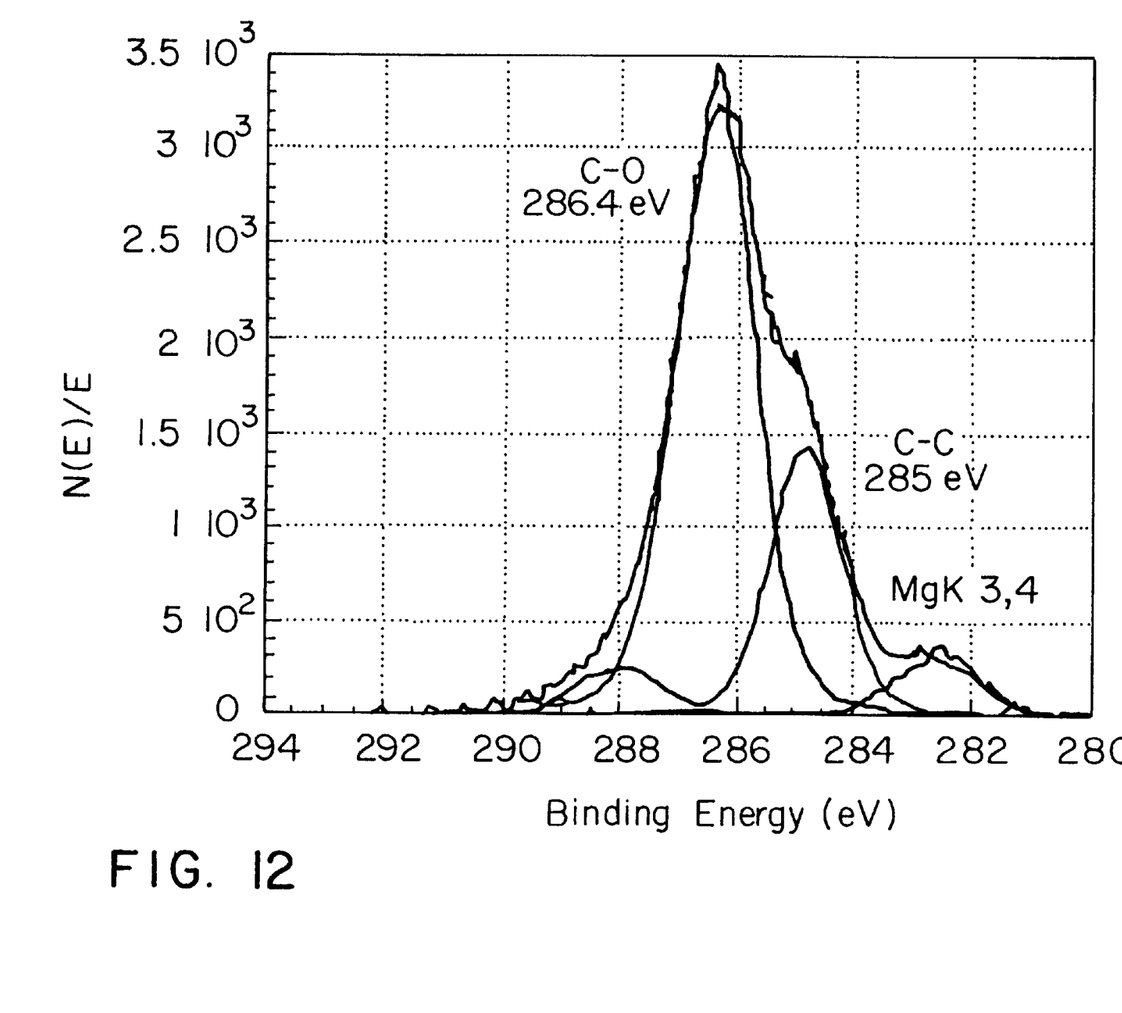
FIG. 12 is a high resolution C1s ESCA spectrum of 12-crown-4-ether-plasma coated stainless steel as in FIG. 9.

Survey (FIGS. 9 and 10) and high resolution (FIGS. 11 and 12) data show that proper selection of the plasma parameters (base pressure: 17 mT; temperature of the "monomer: 70–122° C.; temperature of the reaction chamber: 70–120° C.; pressure in the absence of the discharge: 100–150 mT; pressure in the presence of plasma: 140–500 mT; RF-power dissipated to the electrodes: 100 W; reaction time: 10–30 minutes; pulsed-plasma conditions: period –500 $\mu$s; duty cycle: 30%) allow the control of the chemical structure of the depositing layers. These data demonstrate that high concentrations of —$CH_2$—$CH_2$—O— molecular segments can be incorporated into the nascent plasma deposited polymer layers.

Survey ESCA-based relative surface atomic composition (FIGS. 9 and 10) results and high resolution ESCA information (FIGS. 11 and 12) derived from tri(ethylene glycol) dimethyl ether)—and crown-ether-plasma deposited layers on substrates that were cleaned with detergent prior to plasma deposition (30 minutes of plasma deposition), clearly indicate that these precursors can efficiently deposit under pulsed plasma environments PEG-type structures. It also has been demonstrated that these layers can significantly reduce bacterial attachment, as shown in Table 1 below. The unmodified and plasma treated samples were subjected to one-hour bacterial attachment and one-day biofilm development in a mixed culture. Attached bacteria and bacterial biofilm were removed from the surface and enumerated by plating on typtic soy agar. In addition, biofilm bacteria are more easily removed from the tri (ethylene glycol) dimethyl ether—and crown-ether-plasma coated surfaces as compared to the untreated surfaces.

TABLE 1

| 12-Crown-4-ether-plasma coated stainless steel. | | | | |
|---|---|---|---|---|
| Sample | Log CFU/$cm^2$ 1-hour attachment | % decrease | Log CFU/ $cm^2$ 1-day-biofilm | % Decrease |
| unmodified | 5.17 | — | 6.97 | — |
| 12-crown-4 | <2.0 | 99.9% | 6.35 | 76% |

| Tri(ethylene glycol) dimethyl ether-plasma coated stainless steel | | | | |
|---|---|---|---|---|
| Sample | Log CFU/$cm^2$ 1-hour attachment | % decrease | Log CFU/ $cm^2$ 1-day-biofilm | % Decrease compared to unmodified surfaces |
| unmodified | 5.17 | — | 6.97 | — |
| triglyme | 4.59 | 74% | 6.21 | 83% |

As a further example of the invention, stainless steel samples were treated as described above with an initial oxygen plasma treatment for 15 minutes (continuous wave) followed by 12-Crown-4 ether monomer source plasma coating for 15 minutes. Treated and untreated samples were tested for bacterial attachment as described above, and the results are given in Table 2 below.

TABLE 2

| Sample | Log CFU/$cm^2$ 1-day biofilm | % decrease compared to unmodified |
|---|---|---|
| Unmodified | 7.74 | — |
| Oxygen/12-crown-4 | 7.25 | 67.6 % |

Thus, several objectives are achieved in accordance with the invention by exposing contaminated surfaces to $O_2$-RF plasma environments and subsequently depositing PEG-like structures on various substrate surfaces. The first step provides an $O_2$-plasma-mediated, single-step, dry process for passivation of various inorganic and organic surfaces. Furthermore, thick surface contaminant layers are converted into C—C—O based cross-linked, extremely adherent networks. Subsequent deposition of tri(ethylene glycol) dimethyl ether- and crown-ether-origin anti-fouling layers on oxygen-plasma treated surfaces substantially reduces bacterial attachment to various substrates (e.g., stainless steel). In addition, these processes naturally provide sterilization and partial etching (removal) of the environment-origin biological contamination layer. These results are obtained without the need for wet chemistry based deposition of PEG or polysaccharides to provide a protective polymer film.

Figures 13, 14:
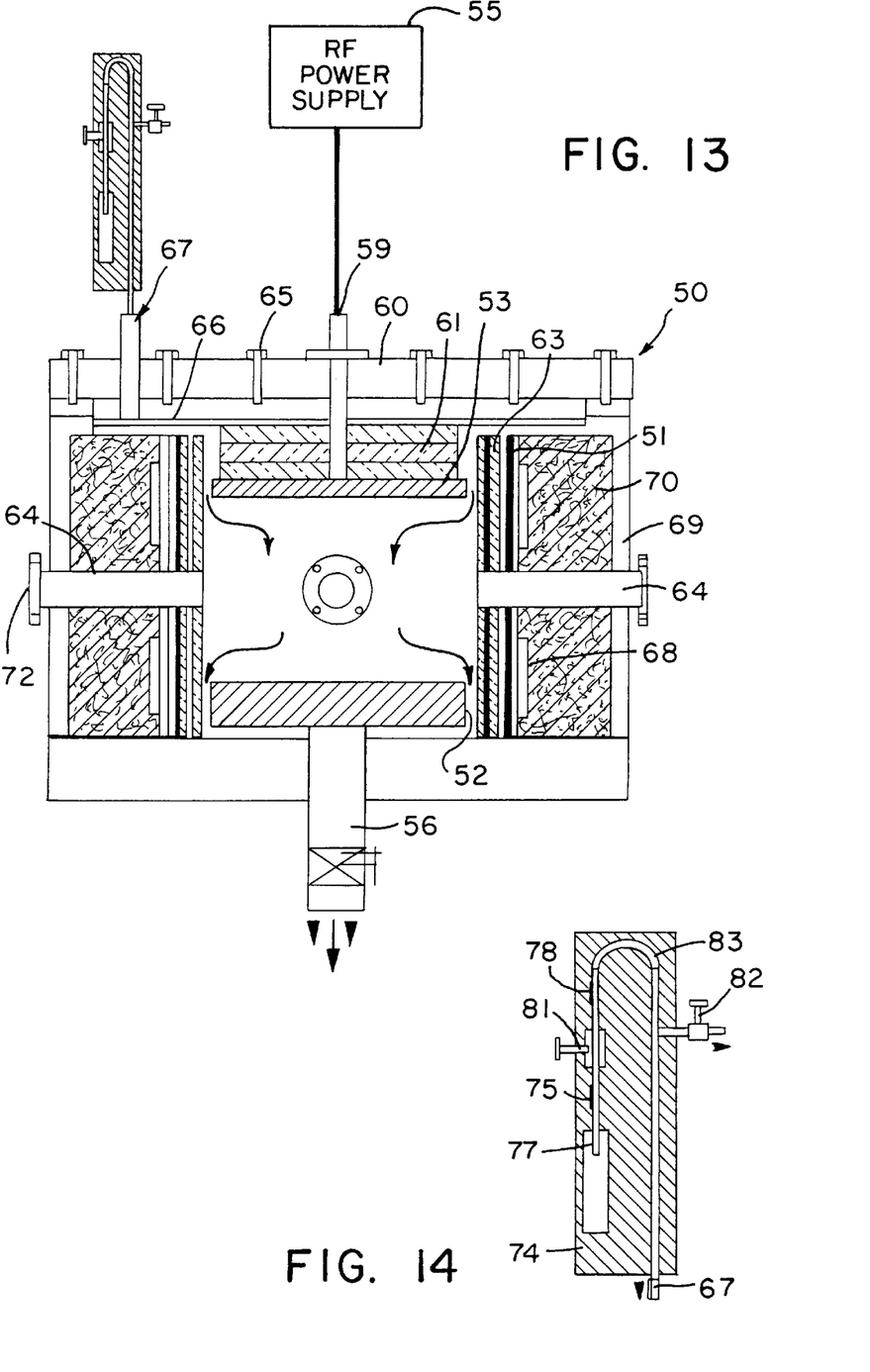
FIG. 13 is a cross-sectional view of a preferred parallel plate plasma reactor provided with heating capabilities.
FIG. 14 ore detailed cross-sectional view of a portion of the reactor of FIG. 13.

A preferred parallel plate reactor with thermostatting capabilities for plasma treatment in accordance with the invention and for optimal deposition of plasma polymers is shown at 50 in FIG. 13. The reactor 50 is provided with heating capabilities (in the range of 25–500° C.) for the reaction chamber, the monomer reservoir, and the connecting stainless steel supply line. The reactor is composed of a cylindrical stainless steel reaction chamber 51 in which a 20 cm diameter and a 0.8 cm thick lower, grounded electrode 52 and an (identical dimensions) upper, stainless steel electrode 53 are located. The upper electrode 53 is connected to a conventional RF-power supply 55. Conventional power supplies are available at 40 kHz, and 13.56 MHz. Typically, the MHz and kHz power supplies are separate units. Both electrodes are preferably removable, which facilitates post-plasma cleaning operations. The lower electrode 52 is also a part of the vacuum line 56 through supporting conically shaped and circularly-perforated stainless steel tubing. The evacuation of the chamber 51 is performed uniformly through the narrow gap (3 mm) existing between the lower electrode 52 and the bottom of the reaction chamber. The upper electrode 53 is directly connected to the threaded end of the vacuum-tight metal/ceramic feedthrough 59 which assures both the insulation of the RF-power line from the reactor and the dissipation of the RF-power to the electrodes. The space between the upper electrode and the upper wall 60 of the reaction chamber is occupied by three 1 cm thick and 20 cm diameter Pyrex-glass removable disks 61. These discs insulate the electrode from the stainless steel top of the reactor and allow adjustment of the electrode to electrode gap. The reactor volume located outside of the perimeter of the electrodes is occupied by two Pyrex-glass cylinders 63 provided with four symmetrically located through-holes 64 for diagnostic purposes. This reactor configuration substantially eliminates the non-plasma zones of the gas environment and reduces considerably the radial diffusion of the plasma species, leading consequently to a more uniform plasma-exposure of the substrates being treated. As a result, uniform surface treatments and deposition processes (6–10% film thickness variation) can be achieved. The removable top of the reactor allows the reaction chamber to be vacuum sealed with the aid of a copper gasket and fastening bolts 65. This part of the reactor also accommodates a narrow circular gas-mixing chamber 66 provided with a shower-type, 0.5 mm diameter orifices system, and with a gas- and "monomer"-supply connection 67. This gas supply configuration assures a uniform penetration and flow of the gases and vapors through the reaction zone. The entire reactor chamber can be heated with electric heaters 68 attached to the outside surface of the chamber. The reactor chamber is enclosed in an aluminum-sheet 69 which protects a glass-wool blanket 70 that surrounds the sides of the reactor chamber to reduce thermal energy loss. Four symmetrically positioned stainless steel porthole tubes pass through the insulating blanket and are connected and welded to the reactor wall for diagnostic purposes. These portholes are provided with exchangeable, optically smooth, quartz windows 72.

The gas reservoir, valve and the connecting stainless steel tubing are shown in greater detail in FIG. 14 and, as shown, are embedded in two shape-designed, 1 cm thick copper jackets 74 provided with controlled electric heaters 75, for processing low-volatility chemicals. The vapor supply assemblage is composed of a reservoir 77, VCR connectors 78, needle valves 81 and 82, and connecting tubing 83. The entire system is insulated using a glass-wool blanket coating.

The plasma reactor 50 is utilized in the same manner as for the reactor system 20 as discussed above, with the added capability of operating with "monomer" materials that are not highly volatile, such as crown ethers, and which require heating to obtain an adequate supply of monomer gas to the reactor chamber. In particular, the reactor 50 may be utilized to control the temperature of the reactor chamber and the substrate so that such low volatility materials do not condense on the substrate but rather are essentially only plasma deposited on the substrate. Such a process allows high quality PEG type films to be formed on substrates that were not obtainable with processes in which the monomer vapor condensed on the substrate as well as being deposited from the plasma.

It is understood that the invention is not limited to the particular embodiments set forth herein as illustrative, but embraces such modified forms thereof as come within the scope of the following claims.

What is claimed is:

1. A method of treating a surface of a substrate that has a film of biological contamination thereon to passivate the surface comprising:
    (a) enclosing the substrate with the surface having a film of biological contamination in a reaction chamber;
    (b) evacuating the reaction chamber to a base level;
    (c) supplying oxygen to and establishing a selected oxygen gas pressure in the reaction chamber; and
    (d) igniting a cold plasma in the gas in the chamber and exposing the substrate surface to the plasma for a selected period of time sufficient to react the oxygen plasma with the biological contamination to form a cross-linked film without etching the film off the surface.

2. The method of claim 1 wherein igniting a plasma in the gas in the chamber is carried out by capacitively coupling RF power to the gas in the chamber.

3. The method of claim 2 including providing capacitive electrodes in the reaction chamber and mounting the substrate with the surface to be exposed to the plasma between the capacitive electrodes, and wherein igniting the plasma in the gas in the chamber is carried out by applying RF power to the electrodes to capacitively couple RF power to the gas between the electrodes.

4. The method of claim 2 wherein the RF power is provided at a frequency of 40 kHz.

5. The method of claim 1 wherein igniting a plasma in the gas in the chamber is carried out by inductively coupling RF power to the gas in the reaction chamber.

6. The method of claim 1 wherein the substrate to be treated is selected from the group consisting of polymers, metals and ceramics.

7. The method of claim 1 wherein exposing the substrate surface to the plasma is carried out for a selected period of time sufficient to sterilize the surface of the substrate and to convert the film of biological contamination into a cross-linked macromolecular network composed predominantly of C—O—C linkages.

8. The method of claim 1 wherein the surface of the substrate is covered by a biofilm which is converted after exposing the substrate to the plasma for the selected period of time to a cross-linked macromolecular network composed predominantly of C—O—C linkages to render the surface of the substrate resistant to adhesion by bacteria and other biological particles.

9. The method of claim 1 including after exposing the substrate surface to the plasma for a selected period of time the further steps of enclosing the substrate with the treated surface in a reaction chamber, evacuating the reaction chamber to a base level, establishing a selected pressure of a gas within the reaction chamber from a monomer source from which a film may be formed having C—O—C linkages, igniting a cold plasma in the gas in the chamber and exposing the substrate surface to the plasma for a selected period of time to provide a plasma mediated film composed of a cross-linked macromolecular network on the surface of the substrate.

10. The method of claim 9 wherein igniting a plasma in the gas in the chamber includes capacitively coupling RF power from an RF power source to the plasma.

11. The method of claim 10 wherein the RF power is coupled in pulses to the plasma in the reaction chamber.

12. The method of claim 10 wherein the frequency of the RF power coupled to the plasma in the chamber is about 13.56 MHz.

13. The method of claim 12 wherein the RF power is coupled in pulses to the plasma in the vacuum chamber.

14. The method of claim 9 wherein the gas supplied to the chamber is from a monomer source selected from the group consisting of ethers, crown ethers, polysaccharides, and poly(ethylene glycol).

15. A method of treating a surface of a substrate that has a film of biological contamination thereon to passivate the surface comprising:

(a) enclosing the substrate with the surface having a film of biological contamination thereon in a reaction chamber;

(b) evacuating the reaction chamber to a base level;

(c) supplying oxygen to and establishing a selected oxygen gas pressure in the chamber;

(d) igniting a cold plasma in the oxygen containing gas in the chamber and exposing the substrate surface to the plasma for a selected period of time sufficient to react the oxygen plasma with the biological contamination to form a cross-linked film without etching the film off the surface;

(e) enclosing the substrate with the treated surface in a reaction chamber;

(f) evacuating the reaction chamber to a base level;

(g) supplying a gas to and establishing a selected pressure of the gas within the reaction chamber from a monomer source from which a film having C—O—C linkages may be formed; and (h) igniting a cold plasma in the monomer source-containing gas in the chamber and exposing the substrate surface to the plasma for a selected period of time to provide a plasma mediated film composed of a cross-linked macromolecular network on the surface of the substrate.

16. The method of claim 15 wherein igniting a plasma in the oxygen-containing gas in the chamber is carried out by capacitively coupling RF power to the gas in the chamber.

17. The method of claim 15 including providing capacitive electrodes in the reaction chamber and mounting the substrate with the surface to be exposed to the plasma in the oxygen containing gas between the capacitive electrodes, and wherein igniting the plasma in the oxygen-containing gas in the chamber is carried out by applying RF power to the electrodes to capacitively couple RF power to the gas between the electrodes.

18. The method of claim 17 wherein the RF power is provided at a frequency of 40 kHz for igniting the plasma in the oxygen-containing gas in the chamber.

19. The method of claim 15 wherein igniting a plasma in the oxygen-containing gas in the chamber is carried out by inductively coupling RF power from an RF power source to the gas in the reaction chamber.

20. The method of claim 15 wherein the substrate to be treated is selected from the group consisting of polymers, metals and ceramics.

21. The method of claim 15 wherein exposing the substrate surface to the oxygen-containing gas plasma is carried out for a selected period of time sufficient to sterilize the surface of the substrate and to convert the film of biological contamination into a cross-linked macromolecular network composed predominantly of C—O—C linkages.

22. The method of claim 15 wherein igniting a plasma in the monomer source-containing gas includes capacitively coupling RF power from an RF power source to the plasma.

23. The method of claim 22 wherein the RF power is coupled in pulses to the plasma in the reaction chamber.

24. The method of claim 22 wherein the frequency of the RF power coupled to the plasma in the chamber is about 13.56 MHz.

25. The method of claim 24 wherein the RF power is coupled in pulses to the plasma in the reaction chamber.

26. The method of claim 15 wherein the gas supplied from a monomer source to the chamber is selected from the group consisting of ethers, crown ethers, polysaccharides, and poly(ethylene glycol).

27. The method of claim 15 wherein the monomer source has low volatility and further comprising the steps of heating the monomer source to provide a gas of the monomer source that is supplied to the reaction chamber and heating the reaction chamber and the substrate to inhibit condensation of the monomer source gas on the substrate.

28. The method of claim 27 wherein the monomer source is a crown ether.

29. A method of treating a surface of a substrate to passivate the surface comprising:

(a) enclosing the substrate with the surface to be treated in a reaction chamber;

(b) evacuating the reaction chamber to a base level;

(c) heating a monomer source to provide a gas therefrom and supplying the gas to and establishing a selected pressure of the gas within the reaction chamber, the monomer source providing a gas from which a film having C—O—C linkages may be formed;

(d) igniting a cold plasma in the monomer source-containing gas in the chamber and exposing the substrate surface to the plasma for a selected period of time to provide a plasma mediated film composed of a cross-linked macromolecular network on the surface of the substrate; and (e) heating the reaction chamber and the substrate while exposing the substrate surface to the plasma to inhibit condensation of the monomer source gas on the substrate.

30. The method of claim 29 including providing capacitive electrodes in the reaction chamber and mounting the substrate with the surface between the capacitive electrodes, and wherein igniting the plasma in the gas in the chamber is carried out by applying RF power to the electrodes to capacitively couple RF power to the gas between the electrodes.

31. The method of claim 30 wherein the frequency of the RF power coupled to the gas in the chamber is about 13.56 MHz.

32. The method of claim 29 wherein igniting a plasma in the gas in the chamber is carried out by inductively coupling RF power from an RF power source to the gas in the reaction chamber.

33. The method of claim 29 wherein the substrate to be treated is selected from the group consisting of polymers, metals and ceramics.

34. The method of claim 29 wherein the monomer source is selected from the group consisting of crown ethers, polysaccharides, and poly(ethylene glycol).

35. The method of claim 29 wherein the monomer source is a crown ether.

36. A substrate with a treated surface made in accordance with the method of claim 1.

37. A substrate with a treated surface made in accordance with the method of claim 15.

38. A substrate with a treated surface made in accordance with the method of claim 35.

* * * * *